US006331320B1

(12) United States Patent
Nakahara et al.

(10) Patent No.: US 6,331,320 B1
(45) Date of Patent: Dec. 18, 2001

(54) PROCESS FOR PRODUCING AROMATIC COMPOUNDS BY SUPERCRITICAL WATER TREATMENT

(75) Inventors: Koichi Nakahara, Osaka; Takahisa Fujii, Kyoto; Wataru Miki, Hyogo; Kenzoh Nagami, Osaka; Kunio Arai, Miyagi, all of (JP)

(73) Assignee: Suntory Limited (JP)

( * ) Notice: Subject to any disclaimer, the term of this patent is extended or adjusted under 35 U.S.C. 154(b) by 0 days.

(21) Appl. No.: 09/445,408

(22) PCT Filed: Apr. 9, 1999

(86) PCT No.: PCT/JP99/01896

§ 371 Date: Jan. 12, 2000

§ 102(e) Date: Jan. 12, 2000

(87) PCT Pub. No.: WO99/52841

PCT Pub. Date: Oct. 21, 1999

(30) Foreign Application Priority Data

Apr. 9, 1998 (JP) .................................................. 10-097819

(51) Int. Cl.[7] .................................................. A61K 35/78
(52) U.S. Cl. .............................. 424/725; 162/79; 424/95; 426/52; 426/422; 426/542; 426/592; 426/597; 252/398
(58) Field of Search .................................... 424/195.1, 95, 424/725; 162/79; 426/52, 422, 597, 542, 592; 252/398

(56) References Cited

U.S. PATENT DOCUMENTS

| 4,652,341 | 3/1987 | Prior | 162/79 |
| 4,832,951 | 5/1989 | Chang-Diaz | 424/195.1 |
| 5,043,100 | 8/1991 | Chang et al. | 426/542 |
| 5,102,675 | 4/1992 | Howell et al. | 426/422 |
| 5,258,188 | 11/1993 | Barmentlo et al. | 426/52 |

OTHER PUBLICATIONS

Steven B. Hawthorne et al., Extraction of Organic Pollutants from Environmenmtal Solids with Sub– and Supercritical Water. Anal, Chem. vol. 66, pp. 2912–2920, Sep. 1994.

Tina M. Pawlowski et al. Extraction of Thiabandazole and Carbendazim from Foods Using Pressurized Hot (Subcritical) Water for Extraction: A Feasability Study. J. Agric. Food Chem., vol. 46, pp. 3124–3132, Jul. 1998.

Martin, J.P. et al. In Lignin Biodegradation: Microbiology, Chemistry and Potential Applications. vol. 1, Kirk, T.K.et al.(eds), CRC Press, Boca Raton, Fl. pp. 77–101. Proc., Internat'l Seminar, May 9–11, 1978 at US FP:L, Madison, WI, Book Published in 1980.

*Primary Examiner*—Francisco Prats
*Assistant Examiner*—K. C. Srivastava

(57) ABSTRACT

The present invention provides a process for producing aromatic compounds or polymers thereof from a plant material in a short period of time and by a simple procedure. Concretely, the process treats the plant material with supercritical water or subcritical water to liberate aromatic compounds, which are contained in the plant material, and/or aromatic compounds, which have been generated upon decomposition of components of the plant material, to the outside of the plant material, and isolates the liberated aromatic compounds to produce aromatic compounds or polymers thereof.

12 Claims, 4 Drawing Sheets

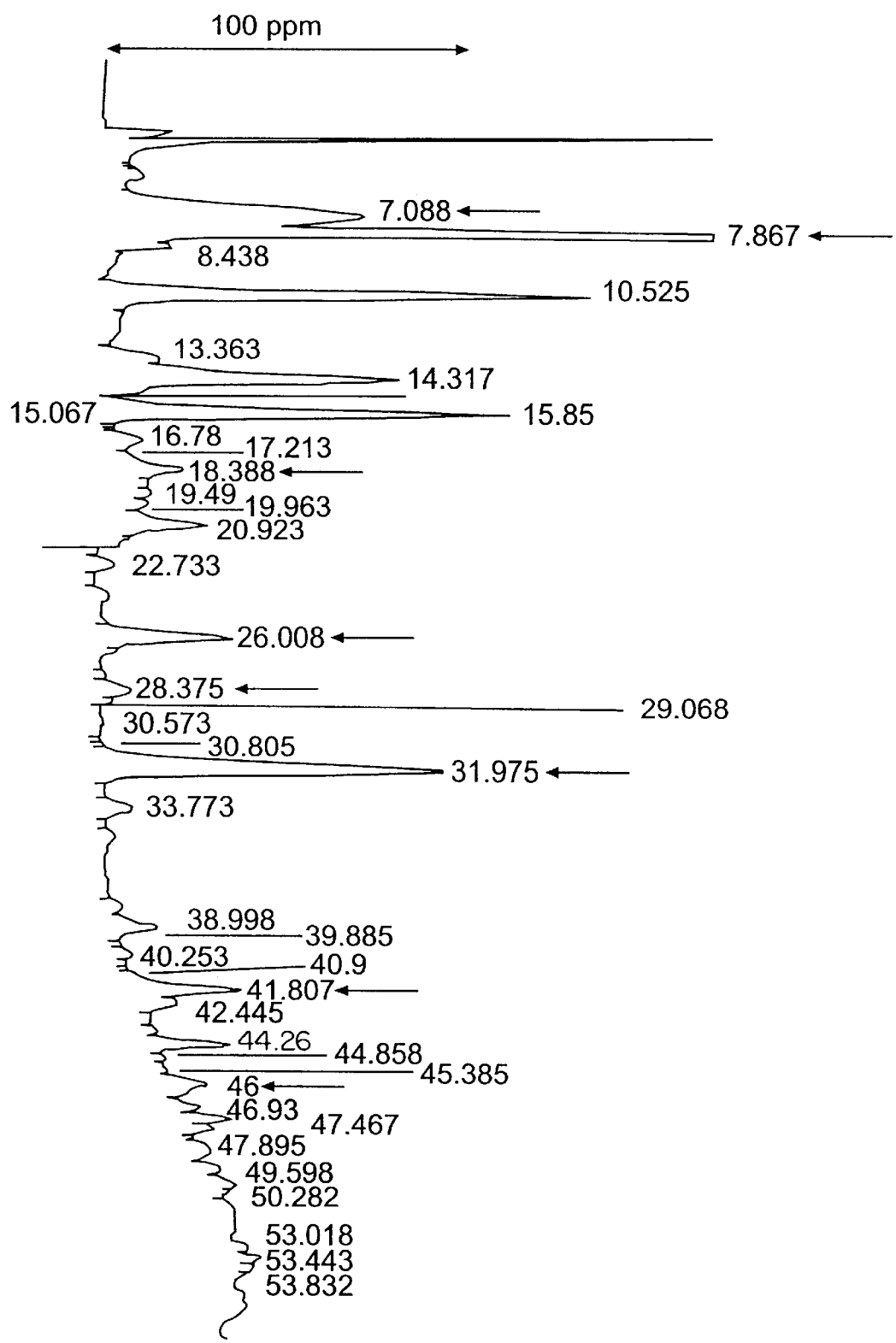
Fig. 1 AROMATIC COMPOUNDS FROM QUERCUS CRISPULA MATERIAL

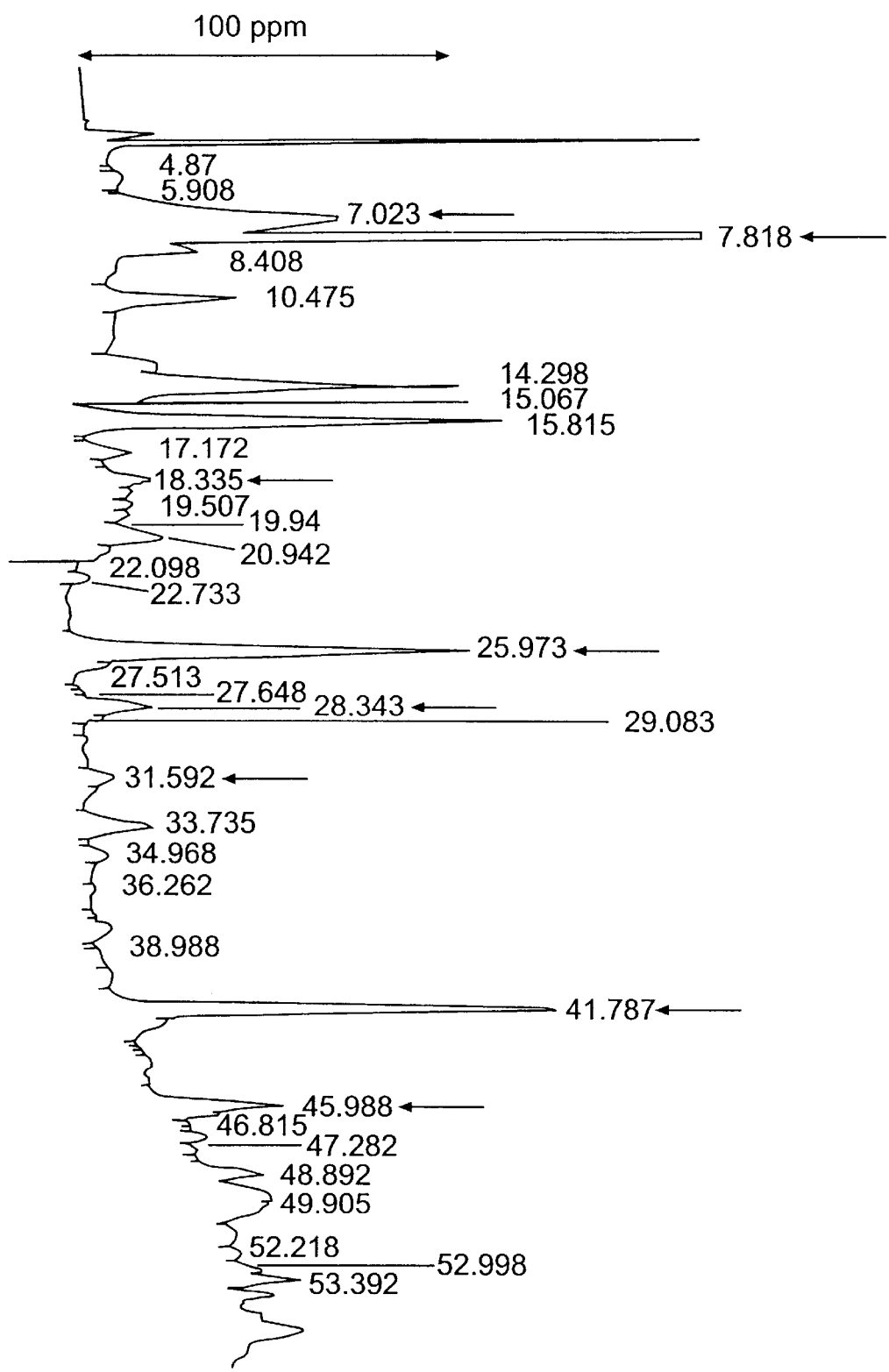
Fig. 2  AROMATIC COMPOUNDS FROM JAPANESE CEDAR MATERIAL

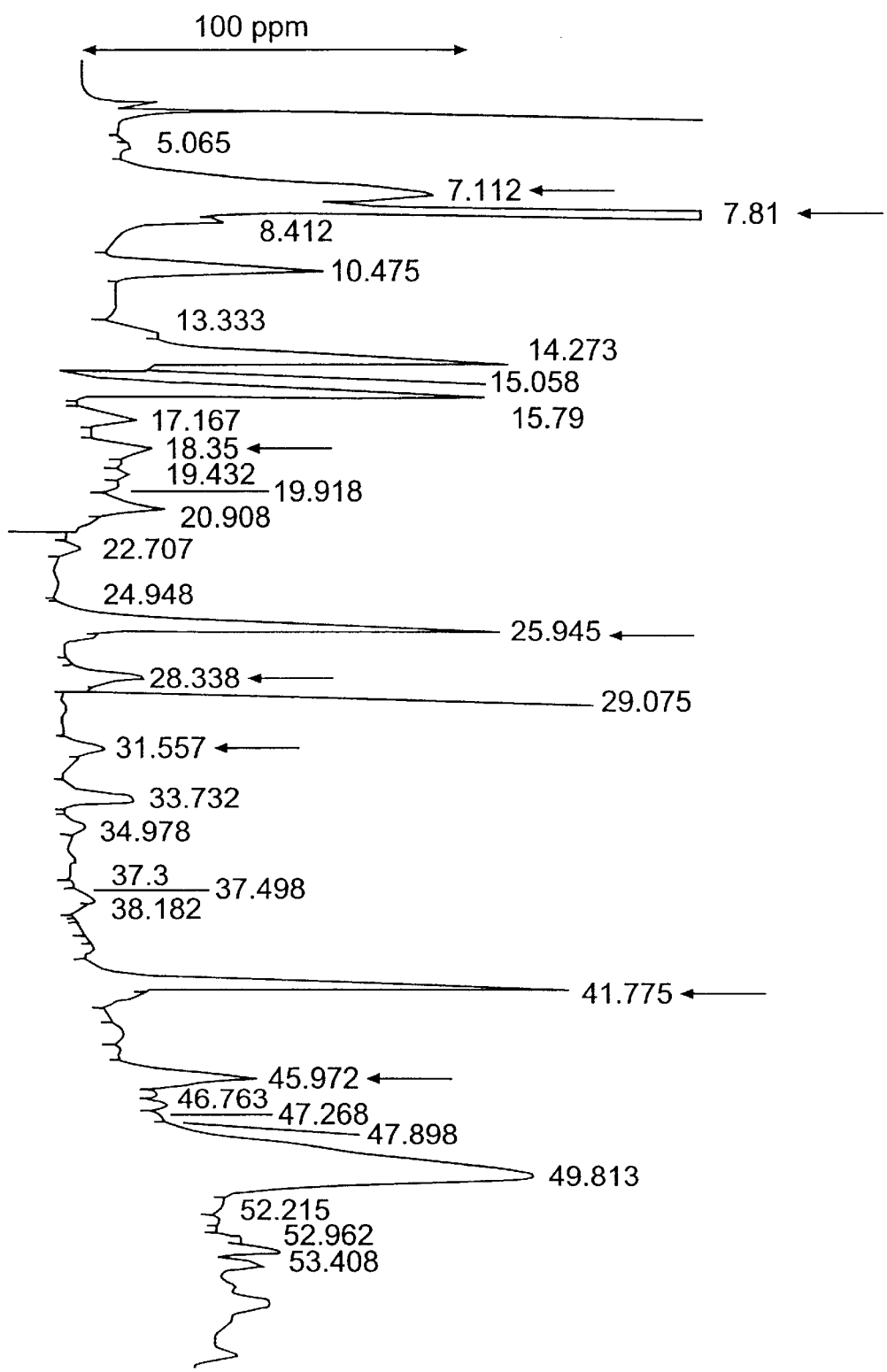
Fig. 3 AROMATIC COMPOUNDS FROM HINOKI MATERIAL

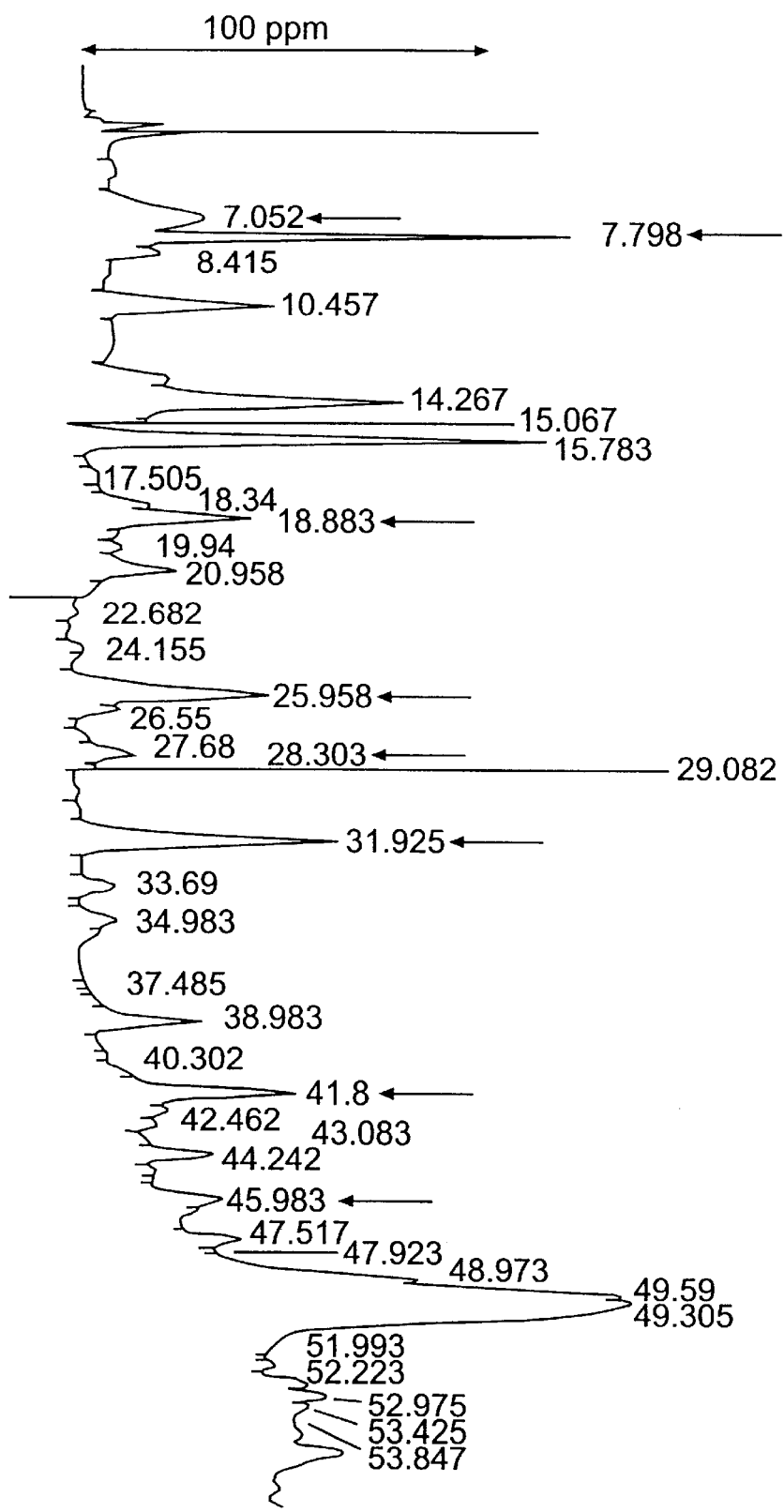
Fig. 4 AROMATIC COMPOUNDS FROM BAMBOO MATERIAL

PROCESS FOR PRODUCING AROMATIC COMPOUNDS BY SUPERCRITICAL WATER TREATMENT

This application is the national phase of international application PCT/JP99/01896 filed Apr. 9, 1999 which designated the U.S.

TECHNICAL FIELD OF THE INVENTION

The present invention relates to a process for producing aromatic compounds from a plant material. More particularly, the invention relates to a process for producing aromatic compounds in a short period of time and by a simple procedure involving treatment of a plant material with water which is in a supercritical state or subcritical state.

PRIOR ART

Plant materials are known to contain polymeric compounds, such as lignin and ellagitannin, having various aromatic compounds, such as vanillin, gallic acid, ellagic acid, and protocatechuic acid, as constituent units. Hitherto known methods for obtaining aromatic compounds contained in plant materials have been only extraction methods involving radical decomposition, such as thermal modification (Japanese Patent Public Disclosure (Kokai) No. 59519/97), electron beam irradiation (Japanese Patent Public Disclosure (Kokai) No. 121392/75), and explosive disintegration (Japanese Patent Public Disclosure (Kokai) Nos. 19895/86, 222802/88, 117400/90, 126725/92, and 145027/92).

Many aromatic compounds have characteristic aromas. Vanillin is an aromatic compound used widely as an edible perfume in foods such as ice cream and candies, and as a flavor in luxury products such as liqueur and tobacco. Industrially, vanillin is synthesized by methylating protocatechualdehyde, which is derived from eugenol or salofural, with an alkali and dimethyl sulfate, or by oxidatively treating lignin sulfonic acid contained in sulfite pulp waste liquor. A method of extraction from vanilla beans is also performed, but can obtain only a trace amount of vanillin from a large amount of a raw material. Syringaldehyde, an aromatic compound, is known as an aroma component of sake, but a method for commercial production of this compound has not been known. Gallic acid is utilized as a deoxidizing agent, a developer for photography, a starting material for inks and dyes, an astringent, or a hemostatic.

Various application studies are under way with regard to extraction, purification, synthesis and decomposition using supercritical fluids. For supercritical water, studies on its capacity to detoxify PCB and dioxin (Japanese Patent Public Disclosure (Kokai) No. 327678/97) are being carried out, and its degradation reaction of biomass is also being investigated. Japanese Patent Public Disclosure (Kokai) No. 31000/93 reports a method which selectively hydrolyzes or pyrolyzes natural or synthetic high molecular compounds with the use of supercritical water as a solvent to decompose the polymers into their constituent units or into approximately oligomeric combinations of the constituent units. Examples of this method include formation of glucose from cellulose contained in large amounts in polymeric resources, such as paper, wood and straw, and conversion of lignin-derived specimens into low molecular compounds. Japanese Patent Public Disclosure (Kokai) No. 268166/97 describes a method for producing various amino acids by hydrolyzing proteins with water present in a supercritical state.

However, it has not been known that it is possible to obtain aromatic compounds by treating plant materials with water present in a supercritical state.

SUMMARY OF THE INVENTION

The present invention provides a process for producing aromatic compounds from a plant material in a short period of time and by a simple procedure.

The present invention further provides a process for producing aromatic compounds, which process does not discharge waste generated as squeeze leavings as results from conventional methods such as thermal modification.

BRIEF DESCRIPTION OF THE DRAWINGS

FIG. 1 is a view showing the results of high performance liquid chromatography of aromatic compounds obtained from a *Quercus crispula* material.

FIG. 2 is a view showing the results of high performance liquid chromatography of aromatic compounds obtained from a Japanese cedar material.

FIG. 3 is a view showing the results of high performance liquid chromatography of aromatic compounds obtained from a hinoki material.

FIG. 4 is a view showing the results of high performance liquid chromatography of aromatic compounds obtained from a bamboo material.

DETAILED DESCRIPTION OF THE INVENTION

The present invention is a process for producing aromatic compounds derived from a plant, or polymers of the aromatic compounds, in a short period of time and by a simple procedure, the process comprising treating a plant material with supercritical water or subcritical water to liberate aromatic compounds, which are contained in the plant material, and/or aromatic compounds, which have been generated upon decomposition of components of the plant material, as individual compounds or polymers thereof to the outside of the plant material; and separating and purifying the liberated aromatic compounds or their polymers.

Aromatic Compounds

The aromatic compounds and their polymers, obtained by the process of the present invention, range variously according to the type of the plant material used. Typical aromatic compounds or polymers thereof include the following:

a) Phenylpropanoids

Vanillin, vanillic acid, coniferyl aldehyde, coniferyl alcohol, syringe, syringic aldehyde, syringic acid, sinapic acid, and polymers of these.

b) Pyrogallol Derivatives

Pyrogallol, gallic acid, ellagic acid, and polymers of these.

c) Pyrocatechol Derivatives

Pyrocatechol, protocatechuic acid, and polymers of these.

Plant Materials Used

The kinds of plants used as starting materials are not restricted, but examples include bamboo, Japanese cedar, hinoki, *Quercus crispula*, cherry tree, Japanese horse chestnut, pine tree, hiba arborvitae, Japanese chestnut tree, bamboo grass, oak, paulownia, Japanese apricot, peach, maple tree, zelkova tree, wisteria, fir, elm, ginkgo, camellia, willow, mulberry, teak, mahogany, magnolia, persimmon, apricot, Chinese quince, sweet brier, rose, loquat, Japanese quince, fragrant olive, camphor tree, Japanese yew, acacia, and prickly shrub of Araliaceae.

In the present invention, any parts of these plants can be used, such as trunk, bark, stalk, branch, root, leaf, flower, bud, and seed. Typically, a woody portion or a floral portion is used. For example, it is preferred to use wooden-type containers which were used for the production and/or storage of fermented products and foods and drinks as plant materials in order to effect utilization of waste materials. Preferably, a plant material is subjected to fine chopping, thin cutting, or powdering as pretreatment to make supercritical water treatment efficient and increase the recovery of aromatic compounds or their polymers.

Conditions for Supercritical Water Treatment

The process of the present invention is characterized by treating a plant material with supercritical water.

It is well known that substances can exist in three states: as a solid, liquid or gas. If temperature and pressure are gradually increased, starting in a state in which a gas and a liquid mingle, when a certain pressure and a certain temperature (i.e., critical point) are exceeded, there exists a range in which the boundary surface between the gas and the liquid disappears, and the gas and liquid integrate as an inseparable entity to form a fluid state. Such a fluid is called a supercritical fluid, which is a high-density fluid having properties intermediate between gas and liquid. That is, this fluid, like a liquid, dissolves various substances, and has high fluidity like a gas.

The critical point for water is a temperature of 374° C. and a pressure of 221 atmospheres. Supercritical water refers to water in a state at a temperature and a pressure in specific ranges exceeding this critical point. Super-critical water continuously varies in the values of parameters, such as density, viscosity, dielectric constant, ion product, and diffusion coefficient, depending on temperature and pressure. Solubility, an important parameter for a reaction solvent, is known to increase as density increases. Another factor related to solubility is dielectric constant, which increases with increasing density, and decreases as temperature rises. At a sufficiently high temperature, a dielectric constant becomes so small that water is almost unable to shield the electrostatic force working among ions. Under these conditions, most of the dissolved ion species are present as ion pairs. Thus, supercritical water behaves as a nonpolar substance, rather than as a polar substance. Incidentally, the pH of water in a supercritical state is 4, producing a hydrogen ion concentration of 1/10,000, while the hydroxide ion concentration is also 1/10,000. Hence, it will be readily apparent that the properties of this water are entirely different from those of water as a liquid.

The present invention produces aromatic compounds by utilizing the foregoing features of supercritical water. Therefore, compared with the conventional technology for producing aromatic compounds from a plant material by thermal modification (Japanese Patent Public Disclosure (Kokai) No. 59519/97), the present invention does not generate by-products which otherwise appear secondarily as a result of a heating method. In this respect, this invention is essentially different from the conventional technology, and can produce aromatic compounds in high yields with ease and in a short time. In light of this feature of the present invention, it can be easily predicted that treatment of a plant material with subcritical water next to supercritical water would similarly be able to obtain aromatic compounds. Hence, references, to be made hereinbelow, to supercritical water also include subcritical water, as will be clear from the context.

During supercritical water treatment, the plant material and water are mixed, for example, at a plant material-to-water ratio of 1:about 1 to 1,000, preferably, 1:about 5 to 200. The reactor may be any container suitable for supercritical water treatment, and may be selected, as desired, according to the scale of production. For example, a closed container (preferably one made of a metal such as SUS alloy) with a capacity of about 1 ml to 10 liters, preferably about 10 ml to 1 liter, is used. This container is charged with about 30 to 40% (V/V), preferably 32 to 35% (V/V), of water, and the plant material is added at the above-mentioned ratio. To produce aromatic compounds, treatment is preferably performed in an anaerobic state. For this purpose, it is advisable to evacuate the inside of the container, or fully purge the inside of the container and water with an inert gas such as nitrogen or argon, followed by closing the container. Treatment is performed under conditions under which water is in a supercritical state at a temperature of about 374° C. (pressure at this time is about 221 atmospheres or more) to about 500° C. (about 300 atmospheres or more), or under conditions under which water is in a subcritical state at a temperature exceeding about 300° C. (exceeding about 150 to 200 atmospheres). The treatment time is within about 30 minutes, preferably within about 2 minutes.

The conditions for the treatment time and temperature are selected from the above-described ranges, according to the plant material used as the starting material, the aromatic compounds intended for production, or various conditions, such as the scale of production. For example, polymers of various aromatic compounds can be obtained by setting a shortened reaction time or a lowered reaction temperature. Concrete conditions for such purposes can be determined easily by experiments.

Separation and Purification of Aromatic Compounds

The plant material treated with water in a supercritical state is cooled by a means such as rapid cooling of the reactor containing the material with iced water or the like. After making sure that the temperature has been sufficiently lowered, the reactor is opened. Normally, water soluble substances are recovered as an aqueous solution, while liposoluble substances adhere to the wall surface of the reactor in a tarry form. Aromatic compounds often show fat solubility, so that the portion adhering to the wall surface is recovered with the use of an organic solvent, such as alcohols, acetone, dimethyl sulfoxide, or acetonitrile. The recovered liposoluble mixture is pretreated, as required, with activated charcoal or an adsorbent carrier. Then, the mixture is used, as such or after separation and purification into respective compound groups or individual compounds in certain cases, according to the purpose of use. Purification methods rely on, but are not restricted to, various chromatographic techniques using silica gel, octadecyl-, cyanopropyl-, or t-butyl-modified silica gel, a cation or anion exchanger, hydrophobic resin, or cellulose as a carrier, electropho-resis, use of various separation membranes, use of various resins, and liquid-liquid distribution.

The tarry substance after extraction of the aromatic compounds is likely to contain other useful components. For example, essential oil components can be isolated by further extraction with hexane-diethyl ether.

The aqueous solution recovered from inside the reactor may contain low molecular compounds such as glucose or lignin. These compounds may be isolated separately, if desired.

EXAMPLE 1

A *Quercus crispula* material was cut thinly with a saw, and powdered. A reactor (internal capacity 10 ml) of SUS alloy was charged with 3.25 ml of distilled water, and 500 mg of the *Quercus crispula* material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds. Then, the reactor was dipped in iced water for cooling. When the temperature of the contents reached 40° C., the reactor was opened. An aqueous solution was removed first, and then a tarry substance adhering to the wall was recovered with the use of ethyl alcohol. The resulting ethyl alcohol solution (about 10 ml) was treated with activated charcoal having a final concentration of 2,000 ppm. The composition of its constituents was examined by high performance liquid chromatography (carrier; Nakarai Tesk ODS reverse phase, mobile phase; 50-minute gradient elution with an aqueous solution containing 2% acetic acid to an aqueous solution containing 2% acetic acid and 25% methyl alcohol, flow rate 1 ml/min, detection wavelength 280 nm).

The results are shown in FIG. 1. The eluted aromatic compounds were used, unchanged, as a mixture, or used as an antioxidant after separation into compound groups or individual compounds by the same column chromatography. The aromatic compounds confirmed were gallic acid, protocate-chuic acid, vanillic acid, syringic acid, vanillin, syringic aldehyde, coniferyl aldehyde, and sinapic aldehyde, in order of increasing retention time (shown by arrows in the drawing).

EXAMPLE 2

A Japanese cedar material was cut thinly with a saw, and powdered. A reactor (internal capacity 10 ml) of SUS alloy was charged with 3.25 ml of distilled water, and 500 mg of the Japanese cedar material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds. Then, the reactor was dipped in iced water for cooling. When the temperature reached 40° C., the reactor was opened. An aqueous solution was removed first, and then a tarry substance adhering to the wall was recovered with the use of ethyl alcohol. The resulting ethyl alcohol solution (about 10 ml) was treated with activated charcoal having a final concentration of 2,000 ppm. The composition of its constituents was examined by high performance liquid chromatography (carrier; Nakarai Tesk ODS reverse phase, mobile phase; 50-minute gradient elution with an aqueous solution containing 2% acetic acid to an aqueous solution containing 2% acetic acid and 25% methyl alcohol, flow rate 1 ml/min, detection wavelength 280 nm).

The results are shown in FIG. 2. The eluted aromatic compounds were used, unchanged, as a mixture, or used as a perfume after separation into compound groups or individual compounds by the same column chromatography. The aromatic compounds confirmed were gallic acid, protocatechuic acid, vanillic acid, syringic acid, vanillin, syringic aldehyde, coniferyl aldehyde, and sinapic aldehyde, in order of increasing retention time (shown by arrows in the drawing).

EXAMPLE 3

A hinoki material was cut thinly with a saw, and powdered. A reactor (internal capacity 10 ml) of SUS alloy was charged with 3.25 ml of distilled water, and 500 mg of the hinoki material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds. Then, the reactor was dipped in iced water for cooling. When the temperature reached 40° C., the reactor was opened. An aqueous solution was removed first, and then a tarry substance adhering to the wall was recovered with the use of ethyl alcohol. The resulting ethyl alcohol solution (about 10 ml) was treated with activated charcoal having a final concentration of 2,000 ppm. The composition of its constituents was examined by high performance liquid chromatography (carrier; Nakarai Tesk ODS reverse phase, mobile phase; 50-minute gradient elution with an aqueous solution containing 2% acetic acid to an aqueous solution containing 2% acetic acid and 25% methyl alcohol, flow rate 1 ml/min, detection wavelength 280 nm).

The results are shown in FIG. 3. The eluted aromatic compounds were used, unchanged, as a mixture, or used as an antioxidant and a perfume after separation into compound groups or individual compounds by the same column chromatography. The aromatic compounds confirmed were gallic acid, protocatechuic acid, vanillic acid, syringic acid, vanillin, syringic aldehyde, coniferyl aldehyde, and sinapic aldehyde, in order of increasing retention time (shown by arrows in the drawing).

EXAMPLE 4

A bamboo material was cut thinly with a saw, and powdered. A reactor (internal capacity 10 ml) of SUS alloy was charged with 3.25 ml of distilled water, and 500 mg of the bamboo material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds. Then, the reactor was dipped in iced water for cooling. When the temperature reached 40° C., the reactor was opened. An aqueous solution was removed first, and then a tarry substance adhering to the wall was recovered with the use of ethyl alcohol. The resulting ethyl alcohol solution (about 10 ml) was treated with activated charcoal having a final concentration of 2,000 ppm. The composition of its constituents was examined by high performance liquid chromatography (carrier; Nakarai Tesk ODS reverse phase, mobile phase; 50-minute gradient elution with an aqueous solution containing 2% acetic acid to an aqueous solution containing 2% acetic acid and 25% methyl alcohol, flow rate 1 ml/min, detection wavelength 280 nm).

The results are shown in FIG. 4. The eluted aromatic compounds were used, unchanged, as a mixture, or used as a perfume after separation into compound groups or individual compounds by the same column chromatography. The aromatic compounds confirmed were gallic acid, protocatechuic acid, vanillic acid, syringic acid, vanillin, syringic aldehyde, coniferyl aldehyde, and sinapic aldehyde, in order of increasing retention time (shown by arrows in the drawing).

EFFECTS OF THE INVENTION

The use of the process according to the present invention makes it possible to obtain useful aromatic compounds or their polymers in a shorter time and with more ease than conventional methods, and in the form of a mixture, compound groups, or individual compounds. Furthermore, by using, as plant materials, barrels after production of alcoholic drinks, materials hitherto handled as waste materials can be utilized effectively. The resulting aromatic compounds or their polymers can be put to a wide variety of uses, such as edible perfumes, flavors for luxury products, and aroma components for Japanese sake. When aromatic compounds are produced by the process of the present invention, moreover, waste as squeeze leavings discharged by conventional methods does not appear. Thus, the invention provides an environmently-friendly technology.

What is claimed is:

1. A process for producing plant-derived aromatic compounds or polymers thereof, comprising heating a plant material, together with water, in a pressurized container at a pressure of 100 to 300 atmospheres and a temperature of 250 to 500° C.; then cooling the inside of the container to about 100° C. or lower; extracting a tarry substance, which has been formed, with an organic solvent selected from the group consisting of alcohols, acetone, dimethyl sulfoxide, and acetonitrile; and isolating aromatic compounds or polymers thereof from the extract.

2. The process of claim 1, wherein the heating is performed at a temperature of 300 to 500° C. and a pressure of 150 to 300 atmospheres to obtain aromatic compounds in a non-polymeric state.

3. The process of claim 1, wherein the heating is performed at a temperature of 250 to 400° C. and a pressure of 100 to 250 atmospheres to obtain aromatic compounds as polymers.

4. The process of claim 1, wherein the heating at a pressure of 100 to 300 atmospheres and a temperature of 250 to 500° C. is performed for 30 minutes or less in an anaerobic state selected from the group consisting of a state under reduced pressure and a state in an inert gas.

5. The process of claim 4, wherein the heating is performed for 2 minutes or less.

6. The process of claim 4, wherein the plant material is a woody portion or a floral portion which has been chopped, cut or powdered.

7. The process of claim 5, wherein the plant material is a woody portion or a floral portion which has been chopped, cut or powdered.

8. The process of claim 6, wherein 1 part by volume of the plant material is heated together with 1 to 1,000 parts by volume of water in the pressurized container.

9. The process of claim 7, wherein 1 part by volume of the plant material is heated together with 1 to 1,000 parts by volume of water in the pressurized container.

10. The process of claim 6, wherein 1 part by volume of the plant material is heated together with 5 to 200 parts by volume of water in the pressurized container.

11. The process of claim 7, wherein 1 part by volume of the plant material is heated together with 5 to 200 parts by volume of water in the pressurized container.

12. The process of anyone of claims 1–11, wherein the aromatic compounds are phenylpropanoids, pyrogallol, a pyrogallol derivative selected from the group consisting of gallic acid, ellagic acid and polymers thereof, pyrocatechol, a pyrocatechol derivative selected from the group consisting of protocatechuic acid and polymers thereof, or a mixture of one or more of these compounds.

* * * * *